United States Patent [19]

Carnahan

[11] 4,220,805
[45] Sep. 2, 1980

[54] LINEAR DIMERS OF BISPHENOLS AND METHOD FOR MAKING

[75] Inventor: James C. Carnahan, Schenectady, N.Y.

[73] Assignee: General Electric Company, Schenectady, N.Y.

[21] Appl. No.: 942,956

[22] Filed: Sep. 18, 1978

[51] Int. Cl.² .................... C07C 41/00; C07C 43/20
[52] U.S. Cl. ................................... 568/592; 568/640; 568/641; 568/33; 568/49; 252/404; 252/406; 252/407; 528/196
[58] Field of Search ................. 568/640, 641, 592; 260/607 AR, 609 F

[56] References Cited

U.S. PATENT DOCUMENTS

| | | | |
|---|---|---|---|
| 2,940,852 | 6/1960 | Herrick et al. | 568/592 X |
| 3,205,198 | 9/1965 | Deanin et al. | 568/641 X |
| 3,547,881 | 12/1970 | Mueller et al. | 568/640 X |
| 3,607,947 | 9/1971 | Penfold | 568/640 |
| 3,897,392 | 7/1975 | Haupt et al. | 568/592 X |
| 4,042,566 | 8/1977 | Murphy | 568/640 |

*Primary Examiner*—Bernard Helfin
*Attorney, Agent, or Firm*—William A. Teoli; James C. Davis, Jr.

[57] ABSTRACT

Linear dimers of certain bisphenols are provided by heating together a monocapped bisphenol salt and a certain dihalogenated alkylene or alkarylene compound in the presence of an inert organic solvent. The linear bisphenol dimers are useful as anti-oxidants and intermediates for making polycarbonates, polyesters and block polymers.

9 Claims, No Drawings

LINEAR DIMERS OF BISPHENOLS AND METHOD FOR MAKING

BACKGROUND OF THE INVENTION

The present invention relates to linear dimers of bisphenols which are derived from monocapped bisphenol salts and certain dihalogenated organic compounds and a method for making such materials.

There is described in Barclay, U.S. Pat. No. 3,069,386, aromatic polyformals which are made by the reaction of bisphenol diphenoxide salts and methylene halides to produce low molecular weight polymers of bisphenol units joined together by formal linkages. The phosgenation of Barclay's aromatic polyformals, result in the production of higher molecular weight materials having a wide spectrum of aromatic polyformal blocks joined by carbonate linkages. Barclay does not attempt to isolate any specific aromatic formal blocks having either terminal formal linkages or phenolic linkages.

In my copending application Ser. No. 942,957, filed concurrently herewith and assigned to the same assignee as the present invention, there is described a method and monocapped phenoxide salts made by such method derived from bisphenols having a dihydropyran capped portion and an alkali metal capped portion as shown by the following formula,

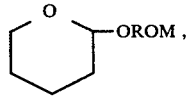 (1)

where R is a $C_{(6-30)}$ divalent aromatic organic radical and M is an alkali metal ion. As described in my aforementioned copending application, the monocapped phenoxide salts of formula (1) are valuble intermediates for introducing bisphenol functionality into a variety of organic materials.

STATEMENT OF THE INVENTION

The present invention is based on the discovery that dimeric bisphenols of the formula, <p align="center">HOROR<sup>1</sup>OROH,     (2)</p> can be made by effecting reaction between a monocapped phenoxide salt of formula (1) and a dihalogenated compound of the formula, <p align="center">R<sup>1</sup>X<sub>2</sub>     (3)</p> in the presence of an inert organic solvent, where $R^1$ is a divalent $C_{(1-12)}$ organic radical selected from alkylene radicals and alkarylene radicals and X is a halogen radical.

There is provided by the present invention a method for making dimeric bisphenols of formula (2) which comprises (1) effecting contact between a phenoxide salt of formula (1) and a dihalogenated compound of formula (3) in the presence of an inert organic solvent at temperatures up to 160° C. to produce a capped bisphenol reaction product, (2) acidifying and agitating the resulting reaction mixture to effect the hydrolysis of the capping group from the reaction product and (3) recovering the bisphenol formal dimer from the mixture of (2).

Radicals incuded by R of formula (1) are, for example, arylene radicals and halogenated arylene radicals, such as phenylene, chlorophenylene, xylylene, tolylene, mesitylidene, etc., and divalent aromatic organic radicals of the formula, $$—R^2QR^2—,$$

where $R^2$ is selected from R radicals and Q is a divalent radical selected from —O—, —S—,

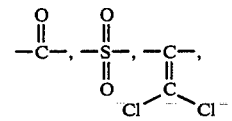

and $—C_yH_{2y}—$, where y is an integer equal to from 1-5 inclusive. Radicals included by $R^1$ are, for example, $C_{(1-8)}$ alkylene radicals, such as methylene, dimethylene, trimethylene, tetramethylene, etc., and alkarylene radicals, such as xylylene, etc.

There are included within the dimeric bisphenols of formula (2), compounds such as

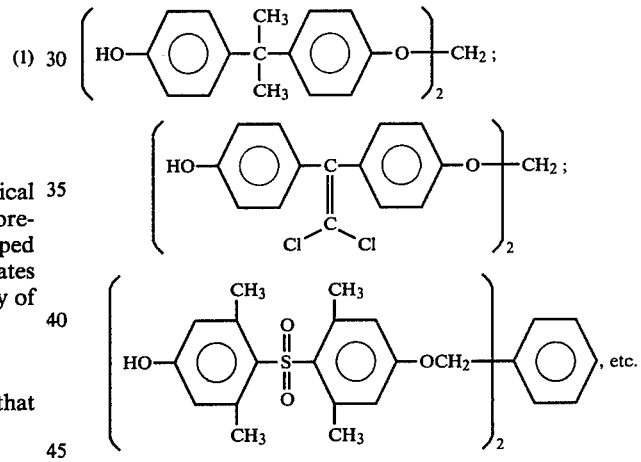

Among the dihalogenated compounds of formula (3), there are included $CH_2Cl_2$, $CH_2ClBr$, $CH_2Br_2$, $CH_2I_2$,

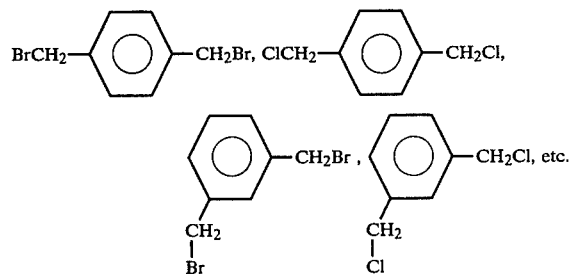

In the practice of the invention the bisphenol dimers of formula (2) can be made by effecting reaction between a monocapped phenoxide salt of formula (1) and a dihalogenated compound of formula (3) in the presence of an inert organic solvent at temperatures in the range of between 25° C. to 160° C. Suitable organic solvents which can be utilized in the practice of the invention are, for example, dimethylsulfoxide, N-methylpyrrolidone, dimethylacetamide, tetrahydrofuran, dimethylformamide, etc. Reaction can be conducted under substantially anhydrous conditions to provide for optimum results, while the order of addition of the reaction is not critical. In order to provide for optimum results, there can be employed an excess of the dihalogenated compound while the mixture is agitated. The formation of the initial reaction product can be obtained in 0.5 to 5 hours, depending upon such factors as the degree of agitation, the nature of the dihalogenated compound, etc.

The reaction product can then be hydrolyzed to the resulting diphenol by acidifying the reaction mixture with an aqueous mineral acid along with agitation. Upon completion of the hydrolysis which can be followed with gel permeation chromatography, the desired bisphenol dimer can be extracted with an organic solvent followed by neutralization of the resulting organic solvent solution. Recovery of the final bisphenol dimer can be achieved by standard recrystallization techniques.

The bisphenol dimers of formula (2) made in accordance with the practice of the present invention, can be utilized as intermediates for making polycarbonates and polyesters, or can be copolymerized with other bisphenols to make copolymers.

In order that those skilled in the art will be better able to practice the invention, the following examples are given by way of illustration and not by way of limitation. All parts are by weight.

EXAMPLE 1

There was added 0.3 part of toluene sulfonic acid to a solution of 57 parts of bisphenol-A and about 300 parts of anhydrous diethylether. After the addition of the condensation catalyst was completed, there was added 21 parts of dihydropyran over a 3 minute period in the form of a 50% solution in diethylether. The reaction was found to be exothermic during the addition and the mixture was refluxed for an additional hour. Analysis of a titer of the mixture with a gel permeation chromatograph showed that the condensation was complete.

There was then added a 25% aqueous solution of sodium hydroxide to the above condensation reaction mixture resulting in the formation of a precipitate. During the addition, the mixture was rapidly stirred. The addition of the sodium hydroxide solution was continued until no further precipitation occurred. The diethylether was then decanted from the mixture and the resulting precipitate was slurried with hot diethylether 3 times and then filtered. The solid filter cake was then washed with additional diethylether and allowed to dry. There was obtained 40.7 parts of the monocapped salt of bisphenol-A having the formula,

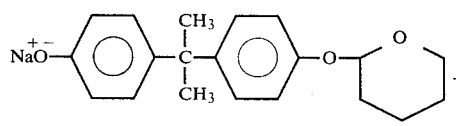

The identity of the above monocapped bisphenol salt trihydrate was established by its C-13 and proton NMR and its IR spectra.

A mixture of 66.8 parts of the above monosodium salt of bisphenol-A monocapped with dihydropyran, 1 part of ground sodium hydroxide, and 240 parts of N-methylpyrrolidone was stirred and warmed to 35° C. to facilitate the dissolution of the various solids. There was then added to the resulting mixture, 212 parts of dichloromethane and the mixture was heated at 50° C. for 1 hour. The mixture was then allowed to cool and there was added about 50 parts of water. The mixture was then acidified with a 20% by weight of aqueous acetic acid to a pH of 6. There was added to the resulting acidified mixture about 100 parts of a 6N hydrochloric acid and the resulting mixture was stirred for 1½ hours at 35° C. After the completion of the hydrolysis of the reaction product, it was extracted into ether and washed with water and sodium bicarbonate until neutral. An oil was formed upon removal of the diethylether. The oil was dissolved in chloroform and the chloroform solution was triturated with hexane resulting in the formation of 36 parts of a white crystalline solid having a melting point of 130°–131.5° C. Based on method of preparation and its NMR and IR. spectra, the product was

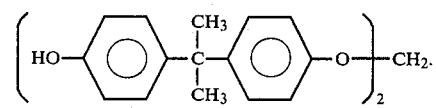

Phosgene was bubbled into a stirred mixture of 100 parts of the above bisphenol linear formal dimer, 0.86 part of p-cumyl phenol, 0.7 part of triethylamine, 700 parts of methylene chloride and 180 parts of water, which had been adjusted to a pH of 11 with a 20% sodium hydroxide solution. The phosgenation was continued for 15 minutes while maintaining the mixture between a pH of 10 and 11 with the addition of added amounts of the sodium hydroxide solution. The phases were allowed to separate and the methylene chloride solution was washed several times with dilute hydrochloric acid, and then with water. The methylene chloride solution was then added to a rapidly stirred methanol resulting in the precipitation of product. The product was recovered by filtration, washed with methanol and dried. There was obtained 90 parts of a formal carbonate consisting essentially of units of the formula,

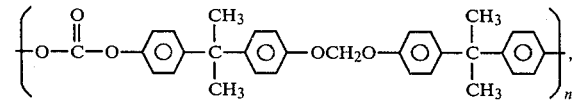

and having terminal units of the formula,

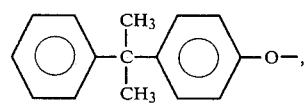

where n has an average value of about 200. The identity of the product was confirmed by its $13_C$ NMR spectrum. The formal carbonate had an intrinsic viscosity of 0.537 in methylene chloride at 25° C. and a glass transition temperature of 100° C. Based on its characteristics, those skilled in the art would know that it was a valuable injection molding material capable of being subjected to temperatures up to 100° C. without suffering a substantial change in shape.

EXAMPLE 2.

There was added 0.3 part of toluene sulfonic acid to a solution of 70 parts of 2,2(4-hydroxyphenyl)1,1-dichloroethylene and about 500 parts of anhydrous diethylether. After the addition of the condensation catalyst was completed, there was added 21 parts of dihydropyran over a 3 minute period in the form of a 50% solution in diethylether. The reaction was found to be exothermic during the addition and the mixture was refluxed for an additional hour. Analysis of a titer of the mixture with a gel permeation chromatograph showed that the condensation was complete.

There was added 25% aqueous solution of sodium hydroxide to the above condensation reaction mixture resulting in the formation of a precipitate. During the addition, the mixture was rapidly stirred. The addition of the sodium hydroxide solution was continued until no further precipitation occurred. The diethylether was then decanted from the mixture and the resulting precipitate was slurried with hot diethylether 3 times and then filtered. The solid filler cake was then washed with additional diethylether and allowed to dry. There was obtained 43.4 parts of the monocapped salt of 2,2(4-hydroxyphenyl)-1,1-dichloroethylene.

A mixture of 8.82 parts of the above monosodium salt of 1,1-dichloroethylidene bisphenol capped with dihydropyran, 1 part of ground sodium hydroxide, 60 parts N-methylpyrrolidone and 53 parts dichloromethane was heated at 70° C. for 1 hour. The mixture was allowed to cool. There was added 100 parts water and the mixture extracted with 100 parts water eight times.

The dichloromethane layer was dried and the solvent removed. The resulting oil was suspended in 80 parts 1:1 ether:methanol and 10 parts 37% aqueous hydrochloric acid was added. The suspension was stirred rapidly at 50° C. for 1 hour. There was added 25 parts of ether and the mixture extracted with water until neutral. The ether layer was dried and the solvent removed. The resulting oil was taken up in chloroform and hexane was added yielding 3.35 parts of a white crystalline solid M.P. 163°–166° C.; recrystallization from chloroform and hexane gave material of M.P. 165°–167° C. Based on the method of preparation and its NMR and IR spectra the product was

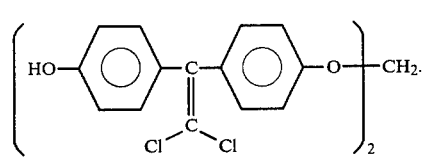

The above material is useful as a flame retardant, an anti-oxidant and as an intermediate for making a polycarbonate in accordance with the procedure of Example 1.

EXAMPLE 3.

A mixture of 66.8 parts of the monosodium salt of bisphenol-A monocapped with dihydropyran of Example 1, 1 part of ground sodium hydroxide, and 240 parts of N-methylpyrrolidone is stirred and warmed to 35° C. There is then added to the resulting mixture, 17.5 parts of α,α'-dichloro-p-xylene and the mixture is heated at 70° C. for 3 hours. The mixture is allowed to cool, water is added and the mixture is acidified with acetic acid. The product is extracted with diethylether, the ether solution dried, and the ether is removed. The mixture is then treated with 1N hydrochloric acid for 5 hours at 40° C. A product is isolated by extraction into diethylether. Based on method of preparation the product is

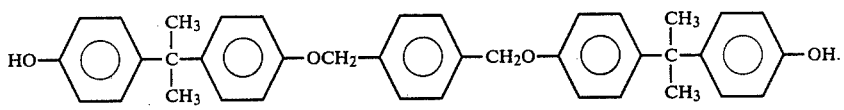

Although the above examples are directed to only a few of the very many variables from which the present invention can be practiced, it should be understood that the present invention is directed to a much broader class of bisphenol dimers shown by formula (2).

What is claimed is:

1. Bisphenols of the formula, $$R^1-(OROH)_2,$$

where R is

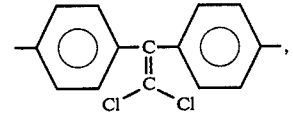

and $R^1$ is selected from divalent $C_{(1-12)}$ alkylene radicals and divalent $C_{(8-12)}$ arylene radicals.

2. The compound

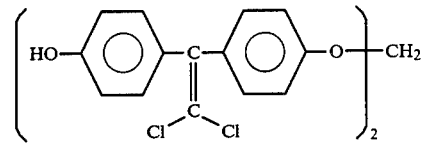

3. The compound

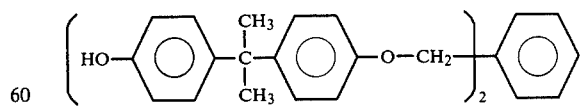

4. A method for making bisphenols of the formula $$R^1-OR-OH)_2,$$

which comprises
(1) effecting contact between a monocapped phenoxide salt of the formula,

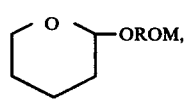

and a dihalogenated compound of the formula,

R¹X₂, in the presence of an inert organic solvent at temperatures up to 160° C. to produce a dicapped phenoxide reaction product, (2) acidifying and agitating the resulting reaction mixture to effect the hydrolysis of the capping group to provide the diphenol reaction product and (3) recovering the bisphenols from the mixture of (2), where R is a $C_{(6-30)}$ divalent aromatic organic radical, R¹ is selected from divalent $C_{(1-12)}$ alkylene radicals and alkarylene radicals, X is halogen and M is an alkali metal ion.

5. A method in accordance with claim 4, where R is

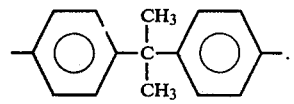

6. A method in accordance with claim 4, where R is

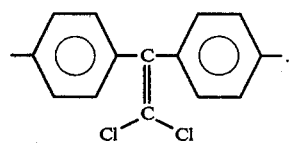

7. A method in accordance with claim 4, where the dihalogenated compound is methylene chloride.

8. A method in accordance with claim 4, where the dihalogenated compound is α,α-dibromxylylene.

9. A method in accordance with claim 4, where M is a sodium ion.

* * * * *